(12) United States Patent
Rusiniak

(10) Patent No.: US 8,800,202 B2
(45) Date of Patent: Aug. 12, 2014

(54) BIOREACTOR

(75) Inventor: Richard J. Rusiniak, Toronto (CA)

(73) Assignee: Converted Carbon Technologies Corp., Toronto (CA)

(*) Notice: Subject to any disclaimer, the term of this patent is extended or adjusted under 35 U.S.C. 154(b) by 477 days.

(21) Appl. No.: 13/023,800

(22) Filed: Feb. 9, 2011

(65) Prior Publication Data

US 2011/0203171 A1    Aug. 25, 2011

Related U.S. Application Data

(60) Provisional application No. 61/302,574, filed on Feb. 9, 2010, provisional application No. 61/346,967, filed on May 21, 2010.

(51) Int. Cl.
*A01H 13/00* (2006.01)

(52) U.S. Cl.
USPC .......................................... 47/1.4; 435/292.1

(58) Field of Classification Search
USPC ................................. 47/1.4; 435/292.1, 289.1
See application file for complete search history.

(56) References Cited

U.S. PATENT DOCUMENTS

| | | | |
|---|---|---|---|
| 7,176,024 B2 * | 2/2007 | Branson et al. | 435/420 |
| 2007/0092962 A1 * | 4/2007 | Sheppard | 435/266 |
| 2010/0162621 A1 * | 7/2010 | Seebo | 47/1.4 |
| 2012/0149091 A1 * | 6/2012 | Wilkerson et al. | 435/257.1 |

* cited by examiner

*Primary Examiner* — Kristen C Hayes
(74) *Attorney, Agent, or Firm* — Tarolli, Sundheim, Covell & Tummino LLP

(57) ABSTRACT

Biomass production apparatus is disclosed and comprises a stack of trays, each tray, in use, being in receipt of a respective layer of liquid, the layers being spaced apart from one another such that each layer has associated therewith a respective headspace. Light sources are provided for each layer and are disposed in the headspace associated with said each layer, to illuminate, at least in part, said each layer.

4 Claims, 4 Drawing Sheets

BIOREACTOR

REFERENCE TO A PRIOR APPLICATIONS

This application claims the benefit of U.S. Provisional Application No. 61/302,574, filed Feb. 9, 2010 and U.S. Provisional Application No. 61/346,967, filed Mar. 21, 2010.

FIELD OF THE INVENTION

The present invention relates to the field of biomass production.

BACKGROUND OF THE INVENTION

Algae is sometimes farmed industrially. In industrial applications, it is known to cultivate algae in shallow outdoor pools or streams which can occupy land areas approaching or even exceeding 300 km$^2$ and which utilize atmospheric carbon dioxide and sunlight as primary inputs.

SUMMARY OF THE INVENTION

A method forms one aspect of the invention and comprises the steps of: providing a plurality of layers of liquid, the layers being disposed in stacked relation to one another; and providing illumination to each of the layers. The method is characterized in that light is introduced between the layers.

According to another aspect of the invention, the layers of liquid can be disposed in stacked, spaced relation to one another and the light can be provided at least in part by light sources disposed in the interstices between the layers.

According to another aspect of the invention, the light sources disposed in the interstices between the layers can be defined, at least in part, by emitters which receive sunlight carried by light tubes.

Apparatus forms another aspect of the invention and comprises a stack of trays and light sources. Each tray, in use, is in receipt of a respective layer of liquid. The layers are spaced apart from one another such that each layer has associated therewith a respective headspace. The light sources are provided for each layer and disposed in the headspace associated with said each layer, to illuminate, at least in part, said each layer.

According to another aspect of the invention, the light sources can be adapted to substantially fully illuminate said each layer throughout the depth of said each layer.

According to another aspect of the invention, the light sources can be defined, at least in part, by emitters which receive sunlight carried by light tubes in use.

According to another aspect of the invention, the light sources can be defined in part by emitters which receive sunlight carried by light tubes in use and can be defined in part by lamps which deliver artificially-produced light.

The apparatus can form part of a production facility which forms yet another aspect of the invention. In addition to the apparatus, the facility comprises: apparatus for introducing, into each tray, carbon dioxide, nutrients and water; apparatus for withdrawing oxygen from each headspace; and apparatus for withdrawing biosolids and water from each tray.

Biomass produced by the method or the facility forms yet another aspect of the invention.

A production facility forms yet another aspect of the invention. This facility comprises: a greenhouse; a plurality of trays disposed in the greenhouse in stacked, spaced relation to one another, each tray having associated therewith a respective headspace, the trays, in use, each containing a layer of water, nutrients, dissolved carbon dioxide and algae; and light sources disposed in the headspaces, each light source illuminating the respective layer beneath.

According to another aspect of the invention, the light sources can be adapted such that, on a dark night, each light source illuminates the respective layer beneath through the full depth of the layer.

According to another aspect of the invention, the light sources can be LED lights.

According to another aspect of the invention, the trays can decrease in size as the stack progresses upwardly.

According to another aspect of the invention, the trays can define a generally conical stack.

According to another aspect of the invention, the tray size and spacing can be such that, over the course of a sunny day, at least the majority of the surfaces of the layers are exposed to sunlight.

Advantages of the invention will become apparent to persons of ordinary skill in the art upon review of the appended claims and upon review of the following detailed description of an exemplary embodiment of the invention, with reference to the attached figures, the latter being briefly described hereinafter.

DETAILED DESCRIPTION

Figure 1:
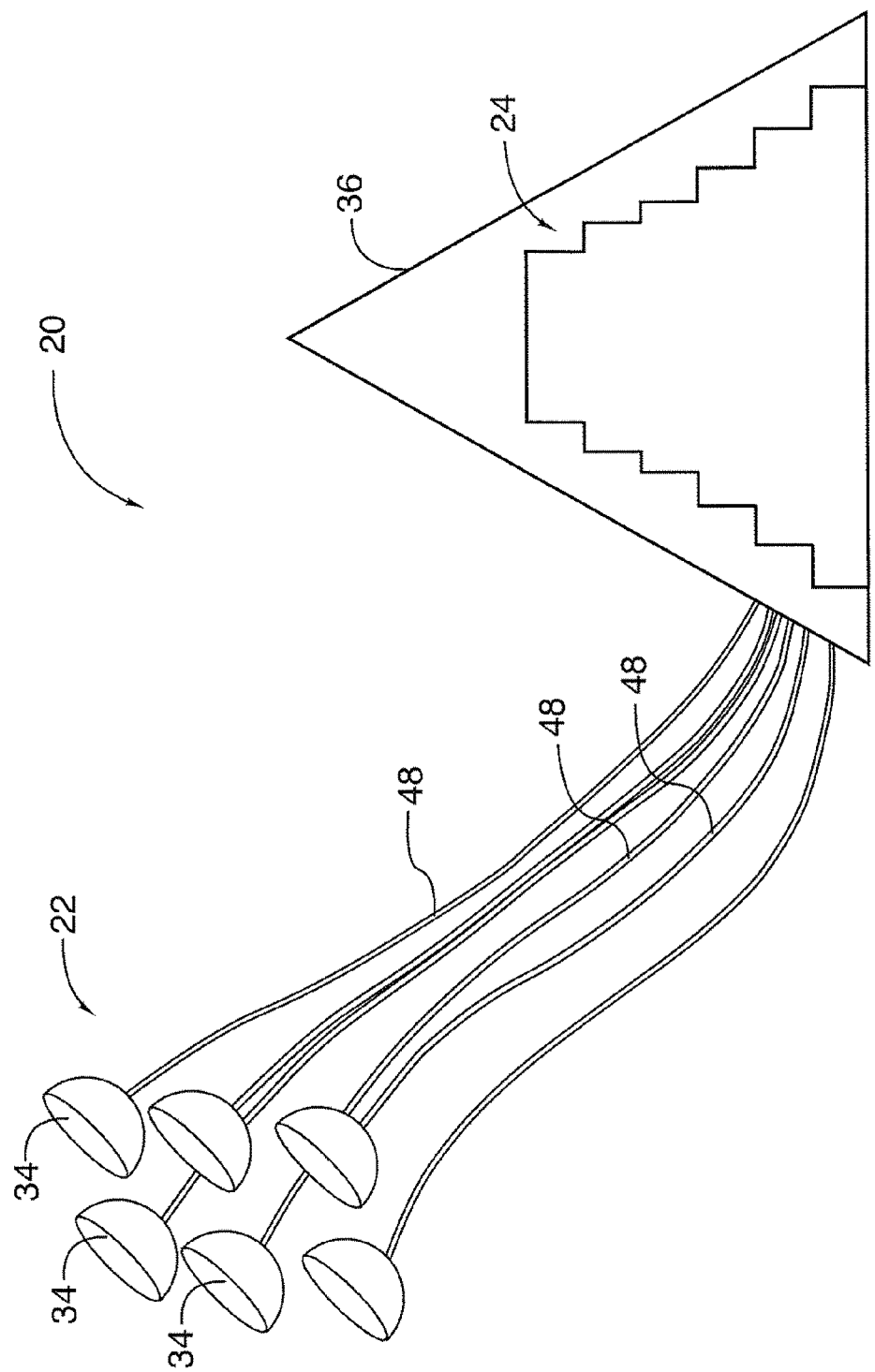
FIG. 1 is a schematic view of a biomass production facility according to an exemplary embodiment of the invention.
Figure 2:
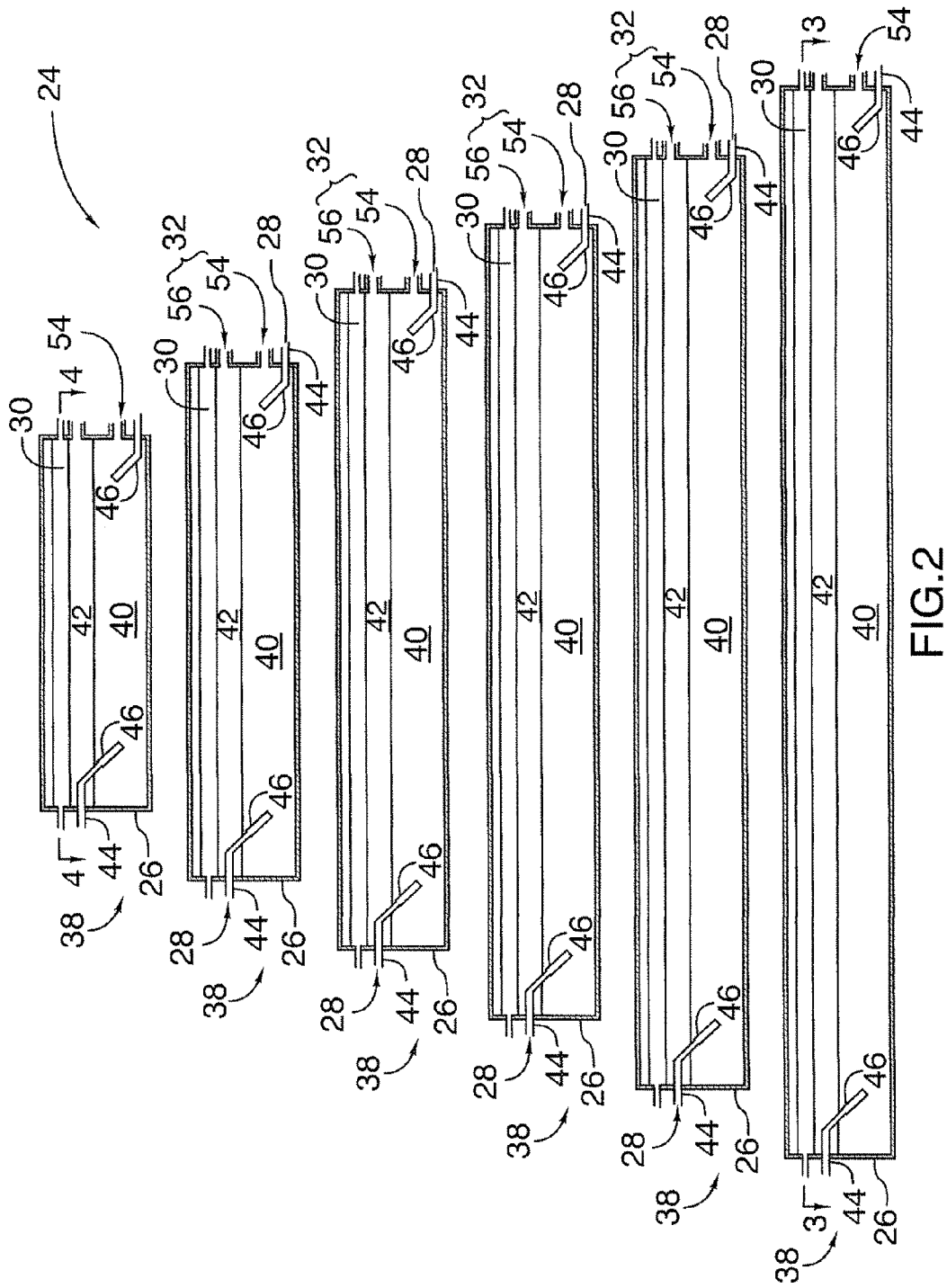
FIG. 2 is a schematic, sectional view of encircled structure 2 of FIG. 1.

An algae production facility 20 according to an exemplary embodiment of the invention is shown in use and in schematic form in FIGS. 1-4 and will initially be understood to comprise an array 22, a conical vessel arrangement 24 including a plurality of walls 26, introduction apparatus 28, light sources 30 and withdrawal apparatus 32.

The array 22 is an array of parabolic solar collectors 34, adapted to gather sunlight.

The vessel arrangement 24 is disposed in a pyramidal greenhouse structure 36.

Walls 26 are made out of translucent or transparent plastic or glass, are vertically-spaced from one another and define a plurality of trays 38. Each tray 38, in use, is in receipt of a respective layer of liquid 40, each layer of liquid 40 having associated therewith a respective headspace 42. The trays 38 vary in diameter to provide the conical shape of the vessel arrangement 24.

Figure 3:
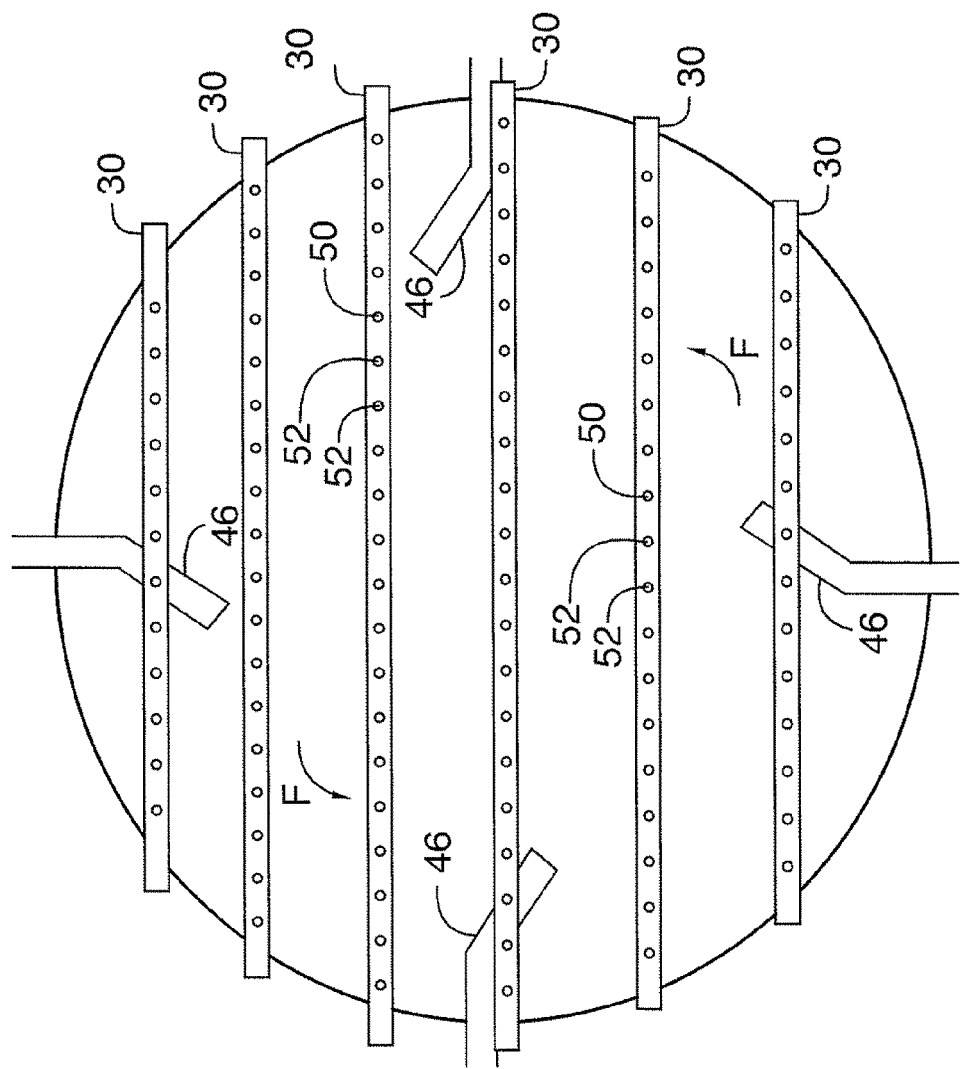
FIG. 3 is a view along 3-3 of FIG. 2.
Figure 4:
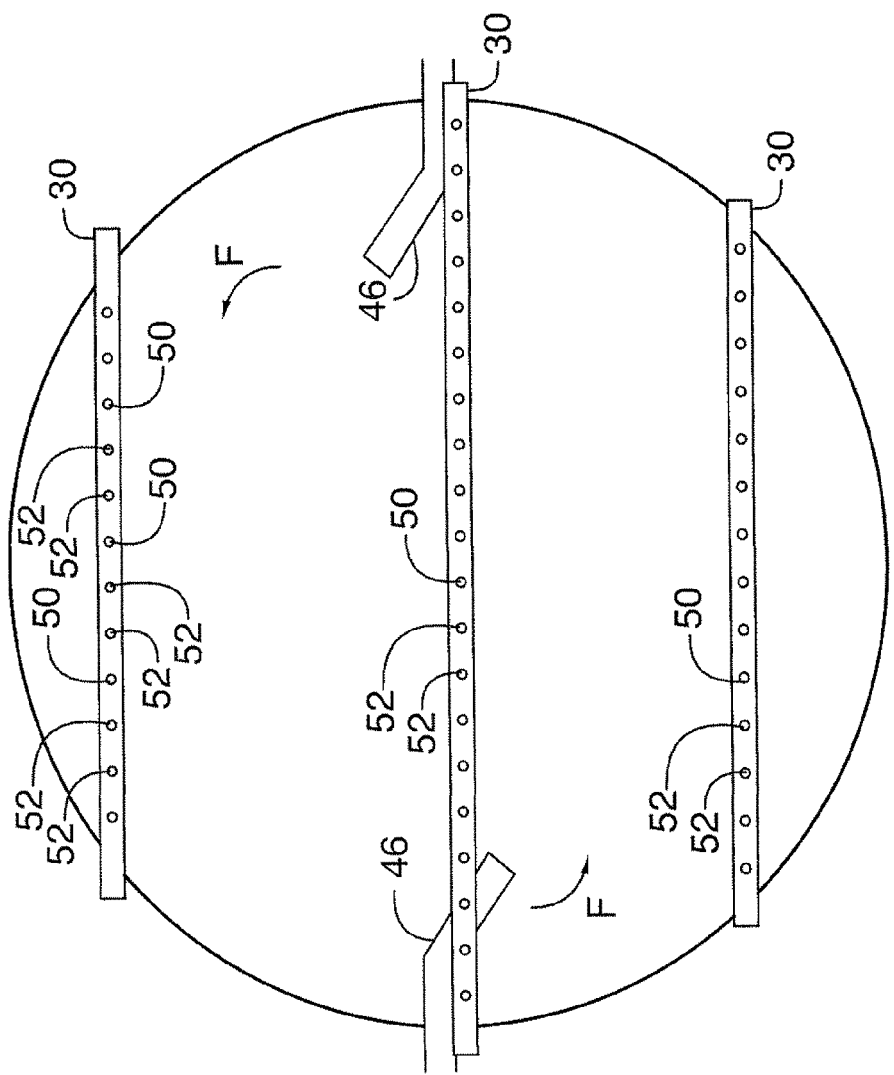
FIG. 4 is a view along 4-4 of FIG. 2.

The introduction apparatus 28 introduces, into each tray 38, carbon dioxide, nutrients and water, and takes the form of piping 44 which enters each tray 38 and terminates, as shown in FIG. 3, in injector nozzles 46 disposed in the layers 40 and orientated to impart a circular liquid flow in said layers 40, as indicated by arrows F, sufficient to promote mixing but with a view to avoiding turbulence, which can be indicative of excess energy consumption. A useful arrangement is to dissolve the carbon dioxide in the water prior to introduction into the tray.

In the illustrations, four nozzles 46 are illustrated in the largest tray and two nozzles 46 are illustrated in the smallest tray, but it will be understood that greater or lesser numbers of nozzles can be provided.

Persons of ordinary skill in the art will readily appreciate the manner in which carbon dioxide, nutrients and water can be introduced via nozzles into a shallow layer of liquid to cause mixing and flow, and as such, further detail is neither required nor provided in this regard.

The light sources 30 are provided for each layer 40 and disposed in the headspace 42 associated with said each layer 40, to, in combination with natural sunlight that reaches the trays through the greenhouse, cause: algal growth; the consumption of carbon dioxide; and the production of oxygen.

The light sources 30 are defined in part by a plurality of light pipes 48 which are coupled to the solar array 22 to bring sunlight collected by the array 22 into the vessel arrangement 24. In the exemplary embodiment, each light pipe 48 terminates in an emitter 50, the emitters 50 being arranged in arrays overlying each layer 40.

Also forming part of the lighting sources 30 is an artificial light source, which illuminates the layers 40 when available sunlight is insufficient to produce algal growth. In the exemplary embodiment, the artificial light source is defined by a multitude of LED lamps 52, also arranged in the arrays.

As a result of the spacing and control of the lamps 52 and emitters 50, the transmissivity of walls 26, the conical shape of the vessel arrangement 24, the mixing provided by the nozzles 46 and the depth of the liquid layers 40, in operation, each layer 40 is substantially fully illuminated throughout the depth of said each layer and, at all times, with an intensity sufficient to promote algal growth. Construction of lighting systems for algae production is a matter of routine to persons of ordinary skill and as such, further detail is neither provided nor required.

The withdrawal apparatus 32 is for withdrawing oxygen and unconsumed carbon dioxide from each headspace 42 and withdrawing biosolids [i.e. algae] and water from each tray 38 and in the exemplary embodiment illustrated takes the form of a plurality of drains 54 and vents 56. Although not shown, persons of ordinary skill in the art will readily appreciate that the material drained from the trays will be dewatered, with the water being filtered and recycled and the dewatered material (i.e. algae) first being sent for oil extraction and thereafter being used for animal feed or ethanol production.

The present arrangement allows for the production of relatively massive amounts of algae and the consumption of relatively large volumes of carbon dioxide. The absence of large surface area, shallow ponds, has advantages in terms of land consumption. The use of natural light has advantage in terms of energy consumption. The use of a reactor vessel rather than outdoor ponds allows for, inter alia, temperature control, to ensure optimal growing conditions, and also avoids contamination. The arrangement could usefully be employed in any locale with an abundance of carbon dioxide, for example, a fossil-fuel powered electrical generation facility.

Whereas but a single exemplary embodiment is herein illustrated and described, it will be evident that changes are possible.

For example, whereas algae growth is specified, this is not essential; the facility can be used for the production of other biomass, such as plankton.

For example, whereas LED lamps are described, other hybrid solar arrangements are possible. One could, for example, place fluorescent tubes in the headspaces, or deliver fluorescent or other light via light tubes or other reflectors.

Further, whereas the vessel arrangement is indicated to be disposed in a greenhouse, it could, for example, equally be situated outdoors and insulated or provided with other heating/cooling facilities as required by the ambient conditions, or situated entirely inside a building and supplied entirely be light pipes and artificial light sources.

As well, whereas parabolic collectors are specified, this is not strictly necessary.

Further, whereas mixing is specified to be provided by nozzles, spaced throughout the trays, other arrangements are possible. For example, a rotating mixing arm could be provided, to provide stirring, and the nozzles could be disposed on the mixing arm itself, to dispense the mixture of carbon dioxide, nutrients and water at controlled PH and temperature.

Additionally, whereas transparent walls are specified, to permit light passage, the walls could be opaque, i.e. made of steel or the like. In this event, to maintain good growth, modification might be required to the liquid depth or the type or placement of the light sources.

Accordingly, the invention should be understood as limited only by the accompanying claims, purposively construed.

The invention claimed is:

1. A production facility comprising:
   a plurality of trays;
   for each tray, a layer of liquid having a surface, each tray being in receipt of the layer for which said tray is provided, the trays being spaced such that each layer has associated therewith a respective headspace; and
   light sources for each layer and which are disposed in the headspace associated with said each layer, to illuminate, at least in part, said each layer,
   wherein the light sources are defined in part, by light pipes which receive sunlight in use, each of said light pipes terminating in an emitter; and
   the light sources are further defined in part by lamps which deliver artificially produced light.

2. A production facility comprising:
   a greenhouse;
   a plurality of trays disposed in the greenhouse in stacked, spaced relation to one another such that each tray has associated therewith a respective headspace;
   a plurality of layers each containing water, nutrients, dissolved carbon dioxide and algae, the layers being provided one for each tray such that each tray is in receipt of the layer provided therefor; and
   light sources disposed in the headspaces, each light source illuminating the associated layer beneath, said light sources comprising LED lights,
   wherein said light sources are adapted such that, on a dark night, each light source illuminates the respective layer beneath through the full depth of the layer; and,
   said trays decrease in size as the stack progresses upwardly.

3. A production facility according to claim 2, wherein the trays define a generally conical stack.

4. A production facility according to claim 2, wherein the tray size and spacing is such that, over the course of a sunny day, at least a majority of the surfaces of the layers are exposed to sunlight.

* * * * *